United States Patent
Arnitz et al.

(10) Patent No.: US 8,540,693 B2
(45) Date of Patent: Sep. 24, 2013

(54) DEVICE FOR SUBSTANTIALLY GERM-FREE PROVISION OF A FLUID MEDIUM

(75) Inventors: Theo Arnitz, Waghäusel (DE); Michael Lammel, Mainz (DE); Tobias Vocke, Bad Dürkheim (DE)

(73) Assignee: F. Hoffman-La Roche AG, Basel (CH)

( * ) Notice: Subject to any disclaimer, the term of this patent is extended or adjusted under 35 U.S.C. 154(b) by 0 days.

(21) Appl. No.: 13/462,617

(22) Filed: May 2, 2012

(65) Prior Publication Data

US 2013/0006213 A1      Jan. 3, 2013

Related U.S. Application Data

(63) Continuation of application No. PCT/EP2010/066491, filed on Oct. 29, 2010.

(30) Foreign Application Priority Data

Nov. 3, 2009  (EP) ..................................... 09174940

(51) Int. Cl.
*A61B 19/00*      (2006.01)

(52) U.S. Cl.
USPC ............................ 604/414; 604/403; 604/411

(58) Field of Classification Search
USPC ......................................... 604/414, 403, 411
See application file for complete search history.

(56) References Cited

U.S. PATENT DOCUMENTS

| | | | |
|---|---|---|---|
| 6,070,623 A | 6/2000 | Aneas | |
| 6,258,078 B1 | 7/2001 | Thilly | |
| 6,382,442 B1 | 5/2002 | Thibault et al. | |
| 6,957,745 B2 | 10/2005 | Thibault et al. | |
| 2003/0144633 A1 | 7/2003 | Kirchhofer | |
| 2004/0199139 A1* | 10/2004 | Fowles et al. | 604/414 |
| 2007/0173783 A1 | 7/2007 | Haindl | |
| 2008/0027401 A1* | 1/2008 | Ou-Yang et al. | 604/265 |

FOREIGN PATENT DOCUMENTS

| | | |
|---|---|---|
| WO | WO 2005/002649 A1 | 1/2005 |
| WO | WO 2006/027199 A1 | 3/2006 |

OTHER PUBLICATIONS

International Preliminary Report on Patentability, PCT/EP2010/066491, May 18, 2012.

\* cited by examiner

*Primary Examiner* — Leslie Deak
*Assistant Examiner* — Sara Sass
(74) *Attorney, Agent, or Firm* — Bose McKinney & Evans LLP

(57) ABSTRACT

A method for removing a fluid medium from a container. The method comprises providing a removal device with a closed-off, sterilizable interior, with a needle element being held in the interior, the interior being closed off by a perforable sealing element; providing the container which contains the fluid medium, the container having a container wall with a perforable section; connecting the removal device and the container, the perforable section and the perforable sealing element being interconnected such that a protected region is created between the perforable section and the perforable sealing element, the protected region being closed off with respect to the surroundings in a substantially germ-free fashion as a result of the connection; and perforating the perforable sealing element and the perforable section by means of the needle element, the needle element penetrating the protected region.

27 Claims, 7 Drawing Sheets

DEVICE FOR SUBSTANTIALLY GERM-FREE PROVISION OF A FLUID MEDIUM

RELATED APPLICATIONS

This application is a continuation of PCT/EP2010/066491, filed Oct. 29, 2010, which claims the benefit of EP 09174940.8, filed Nov. 3, 2009, both of which are incorporated herein by reference in their entireties.

BACKGROUND

The invention relates to a method for removing a fluid medium from a container, a removal device and a device for providing a fluid medium. Such methods and devices can, in particular, be used in the field of medicine, pharmacology or medical technology for removing and/or providing fluid media from/in a container under sterile or almost germ-free conditions, e.g. fluid media in the form of pharmaceuticals and/or diagnostic products. However, other fluid media may also be used. A particular focus of this disclosure relates to coupling a container containing a pharmaceutical and/or a diagnostic product to an injector for injecting the pharmaceutical and/or diagnostic product into body tissue of a user. However, other applications are also possible.

The prior art discloses a number of devices and methods that can be used to remove fluid media from a container. In many cases, it is of the utmost importance that the coupling is brought about under almost germ-free or even sterile conditions. Thus, for example, pharmaceuticals and/or diagnostic products, e.g. in liquid form, are filled into appropriate containers such as e.g. vials, cartridges, bottles, ampoules, carpules or similar containers under sterile-room conditions.

There often is the need to connect containers filled with the medium to further components under sterile conditions, particularly when applying parenteral medicines but also in the case of other liquid media, such as e.g. diagnostic products. An example of such a connection process that should be mentioned is the application of a sterile needle onto a cone (Luer cone) of a ready-made syringe, generally protected by a cap (tip cap), prior to an injection. The original integrity of the two systems, and hence their sterility, is broken for this brief coupling process. In the process, the risk of microbial contamination is very low, as exemplified by the large-scale use of this application, but it nevertheless still exists. The responsibility for a correct application generally falls to the user, e.g. a patient or a medical practitioner. The remaining risk of microbial contamination in such applications is generally already acceptable because the period of time between breaking the sterility, connecting the individual components and the application, e.g. the injection into a body tissue, is comparatively short and so, during this short period of time, there practically cannot be any growth of microbial contamination at the boundaries of the components to be interconnected.

However, in recent times there has been a noticeable trend to more complex injection systems. In particular, in the meantime, ready-made injection systems have been disclosed and become available, which, as auto-injectors, for example, are built for application by the patient himself or else by a medical practitioner. In the case of such ready-made injection systems, an injector is distributed together with a container filled with the fluid medium, e.g. the pharmaceutical and/or diagnostic product, for example in a packaged state. In the case of such ready-made injection systems, the responsibility for a safe coupling process between the filled container and the injector and/or another type of mechanical device shifts to the producer, and thus it must generally follow a validated production process. As a result of this trend to more complex injection systems there are additional production steps during production as a result of the last-mentioned requirement.

However, in practice it is hardly possible to satisfy these requirements. Thus, more complex injectors generally have a fluidic and/or mechanical system that, for example, comprises one or more needle elements. These may be held in an interior of the injector, which, in principle, can be manufactured under non-sterile conditions. This interior is subsequently closed off and disinfected or sterilized, for example by means of ionizing radiation. At the same time, or with a time offset, the associated container is generally filled and appropriately closed off under sterile-room conditions, for example by means of a septum and/or a stopper. A final assembly of the complex injector without interrupting the sterile-room conditions, i.e. connecting the complex mechanical part of the injector to the container while maintaining sterility, is generally very difficult to ensure for reasons of practicality. Accordingly, there will generally be a break in the sterility of the outer surfaces of the container and the mechanical part of the injector before these components are brought together to form the finished injector. However, the problem arises here that there must either be a further sterilization after bringing together the components—which is detrimental to the fluid media in many cases—or microbial growth must be accepted at the boundaries between the individual components over a number of months, namely while the finished injector is being stored. If the fluid medium is then removed through such a contaminated boundary, for example by this interface being pierced by a needle element, e.g. a cannula, this may lead to significant contamination of the fluid medium during the injection process.

This problem does not occur in the case of simple injectors without a relatively complex mechanical and/or fluidic system, like e.g. auto-injectors based on the principle of the syringe. In the case of such simple injectors, the problem is achieved by virtue of the fact that a sterile syringe, which already comprises an injection needle including a fluid connection, can be filled and/or closed in a single work step.

The prior art has also disclosed attachments for containers, the former containing a needle element and being able to be integrated into e.g. a flange cap of a stopper and/or septum. These attachments, which contain a comparatively simple mechanical system, are for example attached to the container under sterile conditions in a filling system. By way of example, the attachments are covered by a cap, which can later be pulled off during use such that a syringe can be connected to the attachment, by means of which the needle element can pierce into the interior of the container through the septum or through the stopper. Examples of such attachments are disclosed in International Publication No. WO 2006/027199 A1, in U.S. Pat. No. 6,258,078 B1, in U.S. Pat. No. 6,070,623, in U.S. Pat. No. 6,382,442 B1 or in U.S. Pat. No. 6,957,745 B2.

However, such attachments do not solve the above-described problem since these attachments generally have to be kept very simple in terms of their mechanics and therefore, for example, cannot contain relatively complex mechanical and/or fluidic elements such as e.g. pumps or the like because these have to be attached under sterile-room conditions. Moreover, the sterile surroundings are generally only terminated shortly before use.

WO 2005/002649 A1 has disclosed a medical device that can be placed onto a skin surface of a user and comprises a transcutaneous device that is provided under sterile conditions. It describes, inter alia, that a lever construction with a second needle section is held in a compressible sleeve, which lies loosely on an elastomeric septum of a medicine bag that can be penetrated by the needle section.

However, a disadvantage of the construction shown in WO 2005/002649 A1 is that the face of the sleeve and the septum merely lie loosely on one another. Hence, there may be ingress of contaminants, germs or moisture into the space between the sleeve and septum. Accordingly, WO 2005/002649 A1 explicitly describes that an external casing is additionally required after the disclosed device was assembled in order to keep said device in a clean state. This constitutes significant additional complexity and moreover does not provide protection against erroneous operations, for example as a result of a user opening the external casing prematurely and leaving it open for a relatively long period of time. Furthermore, there may be problems with condensation effects, particularly in the case of products that require chilled storage and temperature changes connected thereto, because e.g., even in an external casing, moisture is able to penetrate the space between the sleeve and the septum. Furthermore, as a result of the lever construction shown in WO 2005/002649 A1, the sleeve merely lies loosely on the septum. The bearing face and the weight of the lever, by means of which the sleeve is pressed against the septum, are thus strongly dependent on a positioning and alignment of the entire device. By way of example, if the device is rotated, the lever can move such that the sleeve is even removed from the septum and so there no longer is a bearing face. Hence, simple devices that provide at least largely safe and position-independent freedom from germs, even without complicated measures, would be desirable.

SUMMARY

The present invention provides a method for removing a fluid medium from a container, a removal device and a device for providing, preferably permanently providing, a fluid medium, which at least largely avoid the disadvantages of the known methods and devices of the aforementioned type. In particular, a sterile connection between a removal device and a container containing a fluid medium is provided, which allows almost or substantially germ-free or sterile storage, even over a relatively long period of time, and can also be used in conjunction with complex injection devices.

The proposed method can in particular be carried out using a device according to one or more of the described embodiments, and the device can more particularly be designed to carry out a method according to one or more of the embodiments described in the following text.

A method for removing a fluid medium from a container is disclosed in a first embodiment. Within the scope of this disclosure, removal should be understood to mean a process in which the fluid medium is transferred out of an internal region of the container, e.g. a closed-off interior. Moreover, the removal can also comprise a provision of the fluid medium to at least one further device and/or to at least one further element, e.g. a provision to at least one fluidic element such as e.g. to a tube, to an application device, a needle element or similar elements, after the transfer out of the internal region. The term removal should not comprise one or more further, optionally subsequent, steps, which may develop a therapeutic effect and/or a surgical effect and/or a diagnostic effect, such as e.g. an application of the fluid medium onto or into a human or animal body, in particular an injection of the fluid medium. However, such further steps, which may comprise at least one step selected from a diagnostic, therapeutic or surgical step, may be a component of an overarching method for applying the fluid medium, which may, in addition to the described method for removing the fluid medium, optionally comprise one or more further steps, e.g. one or more steps selected from a diagnostic, therapeutic or surgical step, for example at least one application step in which the removed fluid medium is applied onto or into a human or animal body, for example injected into body tissue of the human or animal body.

The method comprises the following method steps, which can preferably, but not necessarily, be carried out in the illustrated sequence. By way of example, method steps a) and b), as described below, can also be interchanged and/or carried out with a time overlap or at the same time and/or also carried out a number of times or repeatedly. Furthermore, additional method steps not mentioned in the following text may be carried out.

The method steps are as follows:
a) providing a removal device with a closed, sterilizable interior, with at least one needle element being held in the interior, the interior being closed off by at least one sealing element that can be perforated.

By way of example, the removal device can be a component of an injector, more particularly a complex injector, which comprises a fluidic system and/or a drive, e.g. within a housing.

In particular, the injector can be an injector which can remove and/or provide relatively large amounts of fluid medium from/in the container, for example at least 5 ml, preferably at least 10 or even at least 20 ml, with larger amounts also being possible, e.g. 50 or 100 ml or more. However, in principle, other types of injectors can also be implemented according to these teachings, for example injectors that can remove and/or provide an amount of fluid medium that is less than 5 ml.

By way of example, the removal device can be designed to re-dispense the fluid medium, as explained in more detail below, for example via a second needle element, for example into a body tissue of a user. By way of example, this dispensing process may take place over a number of minutes. The removal device can furthermore comprise appropriate drives for driving the removal process and/or the dispensing process.

In general, a closed-off interior should be understood to mean an interior that is closed off such that ingress of germs into this interior is at least slowed-down by a measureable amount compared to an interior open to the surroundings. By way of example, the closed-off interior can be closed off in a completely germ-tight fashion such that ingress of germs into the closed-off interior is prevented entirely. However, an embodiment is also possible in which the closed-off interior is merely closed off such that, as described above, ingress of germs is merely slowed down. By way of example, the closed-off interior can be closed off such that ingress of germs into this interior is, over a period of time of at least one week, preferably at least one month, particularly preferably a number of months, practically prevented or at least slowed down, for example by at least a factor of 100, preferably at least a factor of 1000 and particularly preferably by at least a factor of 10,000 compared to an open interior. By way of example, the interior may, for this purpose, comprise a housing, e.g. a housing made of plastic and/or a housing with one or more sealing elements.

In principle, a needle element should be understood to mean any element that is designed to pierce through the sealing element and/or the section that can be perforated of a container, which is described in more detail below, with this also being able to comprise cutting processes in addition to piercing processes. In particular, the needle element can be wholly or partly embodied as a cannula and/or connected to a cannula. However, in principle, other embodiments are also possible.

Here, a sealing element that can be perforated should, in principle, be understood to mean any element that closes off the interior, more particularly closes off the latter in a germ-tight fashion, and can be pierced by the needle element. In particular, the sealing element that can be perforated can, to this end, be embodied in a malleable fashion. By way of example, the sealing element that can be perforated may be wholly or partly made of a plastic that can be pierced by the needle element, for example, it may be made of an elastomer and/or a thermoplastic or thermosetting material. In particular, the sealing element that can be perforated can, as will be explained in more detail below, comprise a film element. Alternatively, or in addition thereto, the sealing element that can be perforated can also for example comprise a stopper and/or another type of sealing element.

b) providing a container which contains the fluid medium, the container having at least one container wall with at least one section that can be perforated.

By way of example, as illustrated above, the fluid medium can be a pharmaceutical and/or a diagnostic product. However, alternatively, or in addition thereto, the fluid medium can also comprise other substances. In particular, the fluid medium can be a liquid. In particular, the embodiments disclosed herein are suitable for high-quality fluid media, more particularly for pharmaceuticals and/or diagnostic products found in the high price range sector. By way of example, the fluid medium may comprise cancer medication.

In principle, the container can be any element that is designed to hold the fluid medium. By way of example, the container may for this purpose comprise a container wall, for example a container wall made of a plastic and/or a glass and/or a metallic material. By way of example, the container may be embodied as a vial or carpule.

As will be explained in more detail below, the fluid medium can be introduced into the container under aseptic conditions, e.g. in a sterile-room, in particular, for example in a conventional filling system under sterile-room conditions. In particular, the container can be designed to maintain sterile conditions in its interior, more particularly in the region of the fluid medium, for a period of time of at least one week, preferably at least one month, particularly preferably a number of months or even years.

The at least one section that can be perforated is a section of the container wall that can be pierced by the needle element. By way of example, the entire container wall can be embodied as a section that can be perforated. Alternatively, it is also possible that merely part of the container wall is embodied as a section that can be perforated. By way of example, the section that can be perforated can in turn comprise a material made of plastic, e.g. an elastomeric, thermoplastic or thermosetting material. In particular, the section that can be perforated can comprise a deformable, e.g. a plastic and/or elastic material. As will be explained in more detail below, the section that can be perforated can for example be embodied as a septum that can be perforated and/or as a stopper that can be perforated.

c) connecting the removal device and the container, the section that can be perforated and the sealing element that can be perforated being interconnected such that at least one protected region, more particularly a permanently protected region, is created between the section that can be perforated and the sealing element that can be perforated, the protected region being closed off with respect to the surroundings in a substantially germ-tight fashion as a result of the connection.

The removal device and the container can for example be connected in a permanent or reversible fashion. By way of example, the removal device can comprise a housing, into which the container can be wholly or partly introduced, with the section that can be perforated and the sealing element that can be perforated being interconnected. However, as an alternative or in addition thereto, the container can also be wholly or partly applied to the removal device from the outside. Provision can be made for one or more holding elements for holding the container on the removal device. In principle, holding should be understood to mean any type of connection in which a relative position between holder and held element is defined by the holder, at least within certain limits. In particular, this may be a fixed holder, e.g. a fixation. In particular, as will be explained in more detail below, the holder can be embodied to bring about holding with a predetermined contact force, i.e. a force with which the sealing element that can be perforated and the section that can be perforated are pressed against one another. By way of example, the holder can be embodied such that a dimension of the protected region and/or the contact force is substantially independent of an orientation of the device and/or the container and/or the removal device. By way of example, the holder can be embodied such that a diameter or equivalent diameter of the protected region does not vary by more than 20%, preferably by no more than 10% and particularly preferably by no more than 5%, independent of an orientation. Alternatively, or in addition thereto, the holder can be embodied such that the contact force for example does not vary by more than 20%, more particularly by no more than 10% and particularly preferably by no more than 5%. The holder can have a detachable design or else be embodied as a holder that is made once or can be made once and is subsequently no longer detachable. In the connected state, the removal device and the container can together form a device which, in principle, can have any design. By way of example, this device can be a device for removal, wherein the removed fluid medium can, for example, be stored and/or dispensed to another device. Alternatively, or in addition thereto, the device can for example also be an injection device, more particularly an auto-injector.

Thus, the sealing element that can be perforated and the section that can be perforated are interconnected during the connection step. This connection can be direct, i.e. as a result of the sealing element that can be perforated being in contact with the section that can be perforated in the connected state. However, alternatively, there may also be an indirect connection, with one or more intermediate elements, such as e.g. one or more seals, being interposed. Exemplary embodiments will be described below. However, a direct application of the section that can be perforated on the sealing element that can be perforated, or vice versa, is particularly preferred.

Within the scope of these teachings, a protected region should be understood to mean a region in which, as a result of the protection by the connection, no germs can enter from the outside, from the surroundings around the removal device and the container, over a period of at least one week, preferably at least one month or a number of months up to one or more years. Such a protected region is also referred to as a permanently protected region. By way of example, this can be brought about by the fact that the connection is brought about in a substantially gap-free fashion, i.e. without any gaps, with it even being possible to tolerate gaps with dimensions of at most 10 µm, preferably at most 5 µm and particularly preferably less than 5 µm, e.g. less than 1 µm, without germs being able to penetrate in any significant number. In particular, the protected region can be delimited locally and be restricted to the surroundings of the region in which, as will be explained in more detail below (method step d)), the needle element penetrates the protected region. Thus, the protected region can for example have a region that is or can be perforated by the needle element and, optionally, a surrounding region that surrounds this region that is or can be perforated, with it being possible for the surrounding region, wholly or partly, to surround the region that can be or is perforated. The surrounding region can accordingly also be minimized, right down to zero.

d) perforating the sealing element that can be perforated and the section that can be perforated by means of the needle element, the needle element penetrating the protected region.

A connection between the interior of the removal device and an interior of the container in which the fluid medium is held is created in this method step. Since this connection is brought about within the protected region, ingress of germs to the needle element is practically impossible during the perforation. Since the protected region is also closed off in a germ-tight fashion prior to the perforation, microbial growth within the protected region is also practically impossible prior to the perforation. Overall, this thus affords the possibility of avoiding the above-described disadvantages, particularly during a relatively long storage of the removal device of the container in a connected state.

Accordingly, after carrying out method step c), there can in particular be a relatively long storage process in a connected state before the perforation process described in method step d) is carried out. As a result of the germ-tight termination of the protected region with respect to the surroundings, both ingress of germs into the protected region and microbial growth within the protected region are preferably substantially avoided during this storage process, which may for example have a duration of a number of months up to at least one year or even a number of years. By contrast, after the perforation carried out in method step d), the fluid medium should be used as quickly as possible, preferably within a week, more particularly within at least one day, particularly preferably within one or more hours.

The described method can be advantageously developed in a number of ways.

The fluid medium can preferably be introduced into the container in sterile surroundings in method step b). The container can subsequently leave the sterile surroundings. By way of example, at least method step c) can subsequently be carried out in non-sterile surroundings. By way of example, this may imply that the fluid medium is introduced into the container in surroundings that are cleaner than the surroundings in which method step c) is carried out, for example in respect of a number of particles of a particular size per cubic meter of air and/or in respect of a number of germs and/or microorganisms per cubic meter of air. Expressed in cleanroom classes, the fluid medium can for example be introduced into the container under a better cleanroom class than the one in which method step c) is carried out, wherein the latter can, more particularly, also take place under ambient conditions, i.e. more particularly not in a cleanroom, for example. By way of example, the introduction of the fluid medium into the container can satisfy a cleanroom condition, for example a condition of a cleanroom of class 100,000 or better. Within the scope of this disclosure, sterile conditions or sterile surroundings can preferably be understood to mean cleanroom conditions with a cleanroom class ISO 3 or better (i.e. at most ISO 3) according to the cleanroom class definition pursuant to ISO 14644-1. However, in principle, cleanroom conditions according to class ISO 6 or better would also be feasible.

At least one processing step can preferably be carried out before carrying out method step c), with, during the processing step, at least one element of the group consisting of an external side of the sealing element that can be perforated, an external side of the section that can be perforated and a space between the sealing element that can be perforated and the section that can be perforated being protected against germ contamination after carrying out method step c). By way of example, this processing step can create a permanently protected region after carrying out method step c), which region may for example also be protected with respect to temperature changes, e.g. during a cooling process, with respect to transportation, with respect to vibrations or with respect to other environmental influences.

This processing step can be brought about in a number of different ways, which can also be combined with one another as desired. Thus, for example, the processing step may comprise at least one disinfection step, with an external side of the sealing element that can be perforated and/or an external side of the section that can be perforated being at least partly disinfected and/or sterilized during the disinfection step. Here, an at least partial disinfection is understood to mean a disinfection of at least a portion, preferably the whole region, of an affected external side. In particular, this is the affected external side of the sealing element that can be perforated and/or the affected external side of the section that can be perforated. Here, the term "affected" should mean the external side that takes part in the formation of the protected region. Here, the external side can be wholly or partly disinfected and/or sterilized.

Here, in general, a disinfection process can be understood to mean a germ reduction process, for example by at least a factor of 10, preferably by at least a factor of 1000 and particularly preferably by at least a factor of 10,000. In particular, this may comprise a sterilization process, i.e. complete removal and/or killing of germs or at least a substantial removal and/or killing of germs, with the germs preferably being encompassed by the sterilization in each development stage. Since, in practice, complete sterilization generally does not succeed with complete certainty, a reduction in the number of microorganisms capable of reproduction by a specific factor (to the power of 10), dependent on the field of application, or a specific probability for complete sterilization is therefore preferably demanded for the sterilization. By way of example, the sterilization can be carried out such that a remainder of microorganisms capable of reproduction in one unit of the sterilized goods is at most $10^{-3}$, preferably at most $10^{-4}$, particularly preferably at most $10^{-5}$ or even $10^{-6}$ colony-forming units. By way of example, the latter means that in one million units of the sterilized goods that underwent the same treatment, there is at most one reproduction-capable microorganism. For the purpose of technical separation between sterilization and disinfection, sterilization generally requires a probability of total sterilization that is greater by one power of ten.

An external side of the sealing element that can be perforated should be understood to mean a side of the sealing element that can be perforated which points away from the interior. Accordingly, an external side of the section that can be perforated should be understood to mean a side of the section that can be perforated which points away from the interior of the container, i.e. for example which points to the surroundings. The external side of the sealing element that can be perforated and/or of the section that can be perforated can be wholly or partly disinfected or sterilized in the process.

The disinfection and/or sterilization can in particular be brought about by means of one or more of the following methods: a thermal disinfection and/or sterilization; a disinfection and/or sterilization by means of ionizing radiation; a chemical disinfection and/or sterilization; a chemical disinfection by means of at least one germicidal means, more particularly silver and/or silver iodide, held in the sealing element that can be perforated and/or in the section that can be perforated. Thus, for example, this can comprise a thermal disinfection and/or sterilization, more particularly a disinfection and/or sterilization in an oven and/or a disinfection and/or sterilization under exposure to infrared radiation. Alternatively, or in addition thereto, there can be a disinfection and/or sterilization by means of ionizing radiation, for example by means of X-ray radiation and/or gamma radiation and/or electron radiation and/or beta radiation. As another alternative or in addition thereto, a chemical disinfection and/or sterilization can comprise a chemical disinfection and/or sterilization. By way of example, this can be a disinfection and/or sterilization by means of at least one suitable chemical, e.g. a disinfectant. By way of example, this can be brought about by simple rubbing of the chemical, e.g. the disinfectant, onto the external side, preferably directly before the section that can be perforated and the sealing element that can be perforated are interconnected. In general, the disinfection and/or sterilization can take place under cleanroom conditions, for example.

In another alternative or in addition thereto, there may be chemical disinfection and/or sterilization by means of at least one germicidal means held in the sealing element that can be perforated and/or in the section that can be perforated. Here, the germicidal means may be contained in a material of the sealing element that can be perforated and/or of the section that can be perforated, for example in a plastic as filler material. Alternatively, or in addition thereto, the germicidal means can also be applied to the sealing element that can be perforated and/or the section that can be perforated in the form of one or more layers. The prior art has disclosed a number of germicidal means. The germicidal means should preferably have long-term stability. The use of antimicrobial materials, such as e.g. silver or silver iodide, is particularly preferred. Various other antimicrobial materials have been disclosed in the prior art.

Accordingly, it is typical for the section that can be perforated and/or the sealing element that can be perforated to have at least one material with a germicidal effect. As explained above, this can for example be brought about by virtue of the fact that these materials themselves have a germicidal effect or have a supporting effect for a disinfection and/or sterilization. As explained above, this can for example be brought about by one or more germicidal means. By way of example, these can be contained in the section that can be perforated and/or the sealing element that can be perforated in the form of loading agents. Alternatively, or in addition thereto, the sealing element that can be perforated and/or the section that can be perforated can, as likewise explained above, be wholly or partly provided with a coating that has a germicidal effect.

In the proposed method, the container can be filled with the fluid medium, and preferably sealed, under almost germ-free conditions, more particularly under sterile conditions, before method step b) is carried out. As illustrated above, this filling can more particularly take place in a filling system, for example a filling line, in a sterile room. After filling and preferably after sealing and before carrying out method step c), the almost germ-free conditions can be interrupted here. In particular, this means that the connection between the container and the removal device need not necessarily be brought about within the sterile room but that there may also be a temporary interruption of the sterile conditions or of the almost germ-free conditions. The interruption of the almost germ-free conditions can be used for further process steps. By way of example, there may be a visual inspection of the containers and/or the removal devices here, for example an inspection in respect of defects and/or contaminations.

As illustrated above, the interior of the removal device should be embodied in a sterilizable fashion. Initially, this means that the container must, in principle, be able to withstand the utilized sterilization conditions and/or make the sterilization possible. The sterilization can be brought about in a number of ways which, in principle, are known to a person skilled in the art and can be utilized individually or in combination. Thus, for example, there may be chemical and/or physical sterilization. By way of example, there can be sterilization by means of at least one germicidal gas, e.g. ethylene oxide. By way of example, the container can for this purpose have such a sterilizable design that the interior for example has at least one inlet opening for the germicidal gas or is designed in another fashion to allow the gas to enter the interior. Here, the container should be embodied such that it withstands the germicidal gas. As an alternative or in addition thereto, there can for example also be sterilization by thermal means, for example by heating and/or by exposure to hot steam. In this case, the container should preferably be embodied in such a sterilizable fashion that it allows the exposure to heat and withstands the latter, for example as a result of using correspondingly thermally stable materials. Furthermore, provision can in turn be made for at least one inlet opening, for example to allow hot steam to enter the interior. As another alternative or in addition thereto, use can also be made of ionizing radiation for the sterilization. By way of example, use can be made of X-ray radiation, gamma radiation, electron radiation or beta radiation or combinations of the aforementioned types of radiation. By way of example, the container can be embodied in such a sterilizable fashion that the latter has materials, e.g. materials made of plastic, which withstand the ionizing radiation but at least partly allow the ionizing radiation to pass for the purpose of disinfecting the interior.

Accordingly, the interior can be disinfected and/or sterilized before carrying out method step a), right up to a complete sterilization of this interior. In the following text, the term disinfection is used such that it comprises at least disinfection and preferably sterilization.

The disinfection and/or sterilization preferably takes place after closing off the interior, that is to say e.g. after an application of the at least one sealing element here that can be perforated on a remaining wall material of the interior. Here, the disinfection, more particularly the sterilization, of the interior can take place in various ways. By way of example, as explained above, there may be thermal disinfection and/or chemical disinfection and/or, and this is particularly preferred, disinfection and/or sterilization by means of ionizing radiation. By way of example, use can, for this purpose, once again be made of X-rays, gamma rays, electron beams, beta rays or a combination of the aforementioned and/or other ionizing rays. Accordingly, the sterilization of the interior need not necessarily take place under sterile conditions but can, for example, be carried out outside of a sterile room since the interior is preferably completely closed off against ingress of germs.

The filled container and/or the disinfected and/or sterilized removal device can also be put into interim storage, which may, in particular, take place under non-sterile conditions. Thus, for example, the container and/or the removal device may be stored under not almost-germ-free conditions before method step c) is carried out. By way of example, an outwardly pointing surface of the section that can perforated and/or of the sealing element that can be perforated can, in the process, be exposed to ambient conditions, more particularly to not almost-germ-free conditions.

As already explained above, the connection between the removal device and the container can more particularly be brought about using one or more intermediate elements. Accordingly, the method can more particularly be embodied such that at least one intermediate element is introduced between the external side of the sealing element that can be perforated and the external side of the section that can be perforated before carrying out method step c), more particularly during the optional processing step, the intermediate element being designed to provide a germ barrier for the protected region after carrying out method step c). Here, the term "before carrying out method step c)" should be interpreted broadly and in principle comprises any sequence of the method by means of which the intermediate element can be introduced between the external side of the sealing element that can be perforated and the external side of the section that can be perforated. By way of example, this introduction of the intermediate element can take place exclusively before the connection. However, alternatively or in addition thereto, the intermediate element can also be wholly or partly introduced during or even after the connection, for example as a result of a connection process taking place at the same time as an introduction of the intermediate element or part thereof. As another alternative or in addition thereto, the intermediate element or parts thereof can also be introduced after the connection by means of a suitable device, for example by means of a syringe or similar devices.

Within the scope of this disclosure, a germ barrier should be understood to mean an element that at least significantly slows down germ contamination of the protected region compared to a case in which no germ barrier is provided. By way of example, germ contamination can be determined and/or quantified by known microbial examinations. By way of example, impression examinations can be carried out at different times and germ contamination can for example be quantified by simple counting of microorganisms. By way of example, germ contaminations of the protected region can be examined after a number of days, a number of weeks, a number of months or even after one or more years. By way of example, the germ barrier can be embodied such that germ contamination after 10 weeks of storing the device is reduced by at least a factor of 2, preferably by at least a factor of 5 and particularly preferably by at least a factor of 10 compared to a connection without a germ barrier.

The intermediate element may comprise one or more elements, which satisfy the aforementioned purpose of providing a germ barrier. In particular, the intermediate element can comprise at least one element selected from the group consisting of an adhesive and a seal, i.e. an adhesive and/or a seal.

If at least one adhesive is introduced, it can act as intermediate element and can provide a germ barrier for the protected region. In the process, the adhesive can for example be applied over a large area such that the protected region is arranged within the adhesive. The needle element then penetrates the adhesive itself during the perforation. However, alternatively, the adhesive can also merely be applied in the region of the germ barrier and merely surround the protected region. By way of example, an adhesive bead can for this purpose be applied to the sealing element that can be perforated and/or to the section that can be perforated before the section that can be perforated and the sealing element that can be perforated are pressed against one another. By way of example, the adhesive bead can have an annular design, for example, in turn, as a circular annulus and/or as a polygonal annulus. In principle, the adhesive may comprise at least one arbitrary deformable material, for example a deformable soft and/or gel-shaped and/or liquid mass. The material may remain in the deformable state or may also be wholly or partly cured. By way of example, but not exclusively, the adhesive may comprise at least one silicone and/or at least one silicone adhesive and/or at least one epoxy resin. If the adhesive is used over a large area, it can preferably, for example in a cured state, be penetrated by the needle element.

As an alternative or in addition to e.g. an adhesive, the intermediate element can, as explained above, comprise at least one seal, which can be introduced between the section that can be perforated and the sealing element that can be perforated and can provide a germ barrier for the protected region. By way of example, the seal can comprise an intermediate element in the form of a gasket ring, e.g. an O-ring. The above-described adhesive bead can also be considered to be such a seal. By way of example, the seal can comprise a material made of plastic, for example a rubber material and/or another elastomeric material. The seal preferably has an at least partly elastic design.

Further embodiments relate to the connection of the section that can be perforated to the sealing element that can be perforated while forming the protected region. Thus, the protected region can for example be formed by virtue of the fact that the section that can be perforated is pressed against the sealing element that can be perforated. In particular, the method can be carried out such that the removal device and the container are connected such that the section that can be perforated and the sealing element that can be perforated are pressed against one another with a defined contact force. Here, a predefined contact force can be understood to mean a contact force that corresponds to a predetermined value, for example with a deviation that does not exceed a predetermined tolerance. By way of example, the predefined contact force may be set, for example set by a user, or else it can be fixedly prescribed. In particular, the predefined contact force can have a substantially constant configuration, for example independent of a position and/or orientation of the removal device and/or the device.

This pressing can be brought about in a direct or else indirect fashion such that the section that can be perforated and the sealing element that can be perforated are in direct contact, or else are in indirect contact via one or more intermediate elements, for example of the aforementioned type. Here, a substantially constant contact force can be understood to mean a contact force which, as explained above, for example varies by no more than 20%, more particularly by no more than 10% and particularly preferably by no more than 5%, in particular after the connection has been established and independently of an orientation of the device and/or of the container and/or of the removal device. For this purpose, use can for example be made of one or more holders which can wholly or partly be a component of the removal device and/or of the container. By way of example, the holder can be embodied such that the container is supported by a housing wall of a housing of the removal device. By way of example, the holder can comprise one or more connection elements of the removal device and/or of the container, for example one or more threads, union nuts, clamps, catches or combinations of the aforementioned and/or other elements. By way of example, the holder may comprise at least one bearing and at least one counter bearing.

Here, within the scope of this disclosure, pressing of one element against another element should also comprise the option of pressing with a reversed contact force. When the section that can be perforated is pressed against the sealing element that can be perforated, a contact region can be created. Here, the protected region can be part of a contact region created during the pressing and can be surrounded by a further part of the pressing region that acts as a germ barrier. In other words, the protected region can be ensured, preferably permanently, by areal pressing, wherein the needle element should thus perforate through the region within which the section that can be perforated and the sealing element that can be perforated are pressed against one another. Alternatively, or in addition thereto, the section that can be perforated can also be pressed against the sealing element that can be perforated, the protected region being surrounded by a contact region created during the pressing. This contact region can in turn act as a germ barrier. An annular pressing can for example be created in this embodiment, for example as a result of the sealing element that can be perforated and/or the section that can be perforated comprising an annular region, for example an annular projection, which is pressed against the respective other sealing element. The protected region then is preferably surrounded by the germ barrier of the contact region in an annular shape, for example in a shape of an annular ring or in the shape of a polygonal ring.

In principle, the above-described options can also be realized in any combination. However, a formation of a germ barrier in the form of areal pressing, in which, as illustrated above, a contact region is created with part of the contact region which surrounds the protected region as a germ barrier, is particularly preferred. Thus, in this case, the sealing element that can be perforated and the section that can be perforated preferably have a direct and immediate contact in the region of the contact region.

As described above, a relatively long period of time can elapse, for example within the scope of storage, between carrying out method step c) and method step d). By way of example, a period of time of at least one week, preferably at least one month and particularly preferably a number of months, or even a period of a year or more, can pass between carrying out method step c) and method step d).

Furthermore, the following method step can be carried out after carrying out method step d), i.e. after carrying out the perforation step:
 e) the fluid medium is wholly or partly transferred into the interior or through the interior from the container.

By way of example, as illustrated above, this transfer can take place by means of the needle element. By way of example, the needle element can, for this purpose, be wholly or partly embodied as a cannula and/or be part of a cannula. However, other transfer options are also feasible. Thus, for example, the removal device can in principle comprise one or more further transfer elements, for example separate tubes and/or other fluid connections, which can for example be wholly or partly introduced into the container through an opening created during the perforation in method step d). Thus, in general, a fluidic connection created in method step d) between the interior and the container can be used to carry out the transfer.

Here, the transfer can be brought about in various ways. Thus, for example, capillary forces and/or gravitational forces can be used for driving the transfer. However, as an alternative or in addition thereto, the transfer can also be actively driven, for example by positive pressure and/or negative pressure, in particular by a negative pressure outside of the container and/or a positive pressure within the container. Thus, for example, the removal device can comprise one or more pumps and/or other types of actuators, which can drive the transfer of the fluid medium from the container into the interior. By way of example, the container can comprise a moveable stopper which is driven into the container interior by means of a drive in order to generate positive pressure in the interior of the container, which positive pressure in turn favors the transfer. Alternatively, or in addition thereto, the removal device can also for example comprise a pump, for example a pump held wholly or partly in the interior, which drives the transfer and for example suctions fluid medium into the interior. Various embodiments are possible. The preferred embodiment where the removal device has at least one actuator for driving the transfer of the fluid medium from the container into the interior allows a comparatively complicated design of the removal device, in contrast to e.g. the above-described prior art. Thus, the removal device need no longer necessarily be produced under sterile conditions because the connection between removal device and container according to these teachings also allows assembly under non-sterile conditions, which is favorable for the use of complex mechanical and/or fluidic components, or may even make this possible for the first time.

Provision can be made for one or more fluidic devices within the interior of the removal device. By way of example, provision can be made in the interior for at least one tube, for example a tube that is connected to the needle element, e.g. a cannula. Other types of fluidic devices can also be provided in the interior.

After the fluid medium was wholly or partly transferred into the interior from the container, it is furthermore possible to carry out the following method step:
 f) the fluid medium is wholly or partly transported out of the interior or through the interior, in particular by means of at least one further needle element and/or a cannula.

The at least one further needle element can be wholly or partly identical to the aforementioned needle element; however, it can also be wholly or partly embodied as a separate needle element. In particular, the further needle element can in turn be wholly or partly embodied as a cannula and/or comprise a cannula. By way of example, the at least one further needle element can be connected to the optional at least one fluidic device in the interior.

By way of example, the transport of the fluid medium out of the interior can take place within the scope of an injection of the fluid medium into a body tissue. By way of example, this injection can take place at the same time as or else with a time offset to the removal of the fluid medium from the container. The transport of the fluid medium out of the interior can once again be driven by one or more actuators. Thus, for example, provision can once again be made for a pump and/or another type of actuator. This at least one optional actuator may also be wholly or partly identical to the at least one optional actuator that drives the transport of the fluid medium into the interior from the container. Thus, for example, as illustrated above, provision can be made for an actuator that drives a moveable stopper into the interior of the container, as a result of which pressure in the interior of the container is increased, as a result of which the fluid medium is transferred to the interior from the container. From there, the same pressure can be used to further transfer the fluid medium out of the interior through the further needle element, for example into a body tissue of a patient. This makes it possible to implement an auto-injector. However, alternatively, another type of removal and/or provision of the fluid medium is also possible, for example the provision not to a body tissue, which itself should not be part of the claimed removal method, but to another device.

The transport during method step f) can once again be through e.g. a sealing element that can be perforated. Thus, for example, at least one further sealing element that closes off the interior can be provided in method step f). This further sealing element can have various designs. By way of example, this further sealing element can in turn be embodied as a sealing element that can be perforated and can for example be perforated by means of a further needle element, for example by means of a further needle element that is a component of the removal device. In principle, this sealing element that can be perforated can have an analogous design to the above-described sealing element. This further sealing element that can be perforated can also have a component design that is wholly or partly identical to the above-described sealing element that can be perforated and can be embodied as separate sealing element that can be perforated. In particular, the further sealing element that can be perforated can in turn comprise at least one film. In respect of further optional embodiments, reference can be made to the above embodiment of the sealing element that can be perforated. As an alternative or in addition thereto, the further sealing element can also have a design that cannot be perforated. Accordingly, the sealing element can for example also have another type of closure that allows a removal of the fluid medium from the interior and/or a transfer of the fluid medium through the interior.

In particular, the further sealing element can be placed onto the skin of a patient, either directly or indirectly, for example via a plaster. It can then optionally be perforated in method step f), with the further needle element penetrating the further sealing element and the skin of the user in order to inject the fluid medium.

In addition to the method in one or more of the above-described embodiments, a removal device and a device for providing a fluid medium are also proposed; these can, in particular, be embodied to carry out a method as per one or more of the above-described embodiments. Accordingly, reference can be made in large parts to the description above in respect of optional embodiments. However, in principle, other embodiments are also possible.

The removal device for providing a fluid medium comprises a closed-off, sterilizable interior, with at least one needle element being held in the interior, the interior being closed off by at least one sealing element that can be perforated, wherein the removal device is designed to be connected to at least one container containing a fluid medium, the container having at least one container wall with at least one section that can be perforated, it being possible to interconnect the section that can be perforated and the sealing element that can be perforated such that at least one protected region is created between the section that can be perforated and the sealing element that can be perforated, the protected region being closed off with respect to the surroundings in a substantially germ-tight fashion as a result of the connection, with, in the connected state, it being possible for the sealing element that can be perforated and the section that can be perforated to be perforated by the needle element such that the needle element penetrates the protected region.

The device for providing the fluid medium comprises at least one removal device of the aforementioned type in one or more of the possible embodiments, i.e. at least one removal device with at least one closed-off, sterilizable interior, with at least one needle element being held in the interior, the interior being closed off by at least one sealing element that can be perforated. Furthermore, the device comprises at least one container containing the fluid medium, the container having at least one container wall with at least one section that can be perforated. The removal device and the container can be interconnected, it being possible to interconnect the section that can be perforated and the sealing element that can be perforated such that at least one protected region is created between the section that can be perforated and the sealing element that can be perforated, the protected region being closed off with respect to the surroundings in a substantially germ-tight fashion as a result of the connection, with, in the connected state, it being possible for the sealing element that can be perforated and the section that can be perforated to be perforated by the needle element such that the needle element penetrates the protected region.

The protected region can, in particular, be locally delimited, for example locally delimited to the surroundings of the region in which the needle element penetrates the protected region. By way of example, the protected region can have a lateral extent, e.g. a diameter and/or an equivalent diameter, which does not exceed 10 mm and preferably does not exceed 5 mm or even does not exceed 3 mm.

In particular, the protected region can be embodied as a permanently protected region. A microbial growth can have been or can be at least largely prevented in the protected region, particularly in the connected state. By way of example, germ contaminations of the protected region can be examined after a number of days, a number of weeks, a number of months or even after one or more years. By way of example, the permanently protected region can be protected such that germ contamination after 10 weeks of storing the device, compared to open storage under the same conditions, e.g. ambient conditions, is reduced by at least a factor of 2, preferably by at least a factor of 5 and particularly preferably by at least a factor of 10.

The proposed device can be advantageously developed in a number of different ways. By way of example, the device can be embodied such that at least one intermediate element is introduced between the external side of the sealing element that can be perforated and the external side of the section that can be perforated, the intermediate element being designed to provide a germ barrier for the protected region after carrying out method step c). Reference can for example be made to the above description in respect of possible embodiments of the at least one intermediate element, which can also be combined as desired. By way of example, the intermediate element can comprise at least one element selected from the group consisting of an adhesive and a seal.

The device can, in particular, be designed to interconnect the removal device and the container in such a way that the section that can be perforated and the sealing element that can be perforated are pressed against one another with a predefined contact force. In respect of possible embodiments of this optional embodiment of the device, reference can be made to the description above.

By way of example, the device can comprise at least one holder that ensures the aforementioned properties, i.e. a holder which is designed to provide the predefined contact force, at least in part. By way of example, this holder can comprise one or more connection elements of the removal device and/or one or more connection elements of the container. In particular, the holder can be a position-independent holder. More particularly, the holder can be designed to permanently ensure the contact force, for example independently of a position and/or orientation of the device.

The section that can be perforated and/or the sealing element that can be perforated can, either individually or both, contain at least one material with at least one germicidal means. In this respect, reference can be made to the description above. By way of example, the germicidal means can be mixed into a material and/or be contained in another fashion and/or be applied onto the sealing element that can be perforated and/or the section that can perforated as a coating. The germicidal means can, in particular, comprise silver and/or silver iodide.

As illustrated above, it is particularly preferred for the section that can be perforated and/or the sealing element that can be perforated to have deformable, more particularly elastic, properties. The sealing element that can be perforated can more particularly comprise at least one sealing film. Here, a sealing film should be understood to mean an element that has sealing properties with respect to germs, which is flexible and the lateral extent of which exceeds its thickness a number of times, preferably at least 10-fold, particularly preferably 100-fold or more. The section that can be perforated can more particularly comprise a stopper and/or a plunger stopper, i.e. a moveable stopper, and/or comprise a septum. However, in principle, other embodiments of the section that can be perforated are also possible.

The removal device can more particularly comprise at least one fluidic device, more particularly a fluidic device comprising the needle element, in the interior. The fluidic device can be designed to transport the fluid medium wholly or partly into the interior and/or through the interior from the container. As illustrated above, the fluidic device can more particularly comprise one or more tubes and/or other types of lines. The fluidic device can also wholly or partly comprise the at least one needle element, for example, by wholly or partly embodying the latter as a cannula.

The fluidic device can furthermore, analogously to the above-described, preferred method, be designed to transport the fluid medium wholly or partly out of the interior, in particular by means of at least one further needle element and/or a cannula. This can in turn more particularly take place by perforating at least one further sealing element that closes off the interior. In this respect, reference can be made to the description above.

The device can furthermore, as illustrated above, comprise at least one actuator. This actuator can more particularly be designed to drive the transfer of the fluid medium into the interior and/or out of the interior from the container. Here, "driving" can in principle mean any influencing of this transfer, preferably an influence that promotes or even forces this transfer. By way of example, these actuators can comprise linear actuators, pumps, tappets or combinations of the aforementioned elements and/or other elements and/or other types of known actuators for driving a fluid medium. The at least one actuator can more particularly be designed to establish a fluid connection between the container and the removal device, for example the interior. In particular, the actuator can be wholly or partly situated in the interior. The actuator can accordingly be designed to be disinfected and/or sterilized with the interior.

As explained above, the device can more particularly be embodied as an auto-injector. Here, an auto-injector should be understood to mean an injector, by means of which there can be a simple injection by a user or a medical practitioner himself by placing it on a body surface of the user, without this requiring manual drawing up of the syringe in advance. By way of example, the device can be stuck onto the skin surface of the user by means of a plaster or in a different way and/or it can be fixed on the skin surface in a different way. In particular, the auto-injector may comprise one or more high-quality medicaments. The auto-injector can more particularly be embodied to be stored for a relatively long time, wherein reference can be made to the aforementioned storage times.

The proposed method, the proposed device and the proposed removal device have a number of advantages over conventional methods and devices of this type. Thus, in particular, it is possible to avoid a complex aseptic process step combination. After production, for example under sterile conditions, or after a disinfection up to a sterilization, the individual components of the device can leave the sterile ambient conditions and can thereafter be further processed and/or stored under usual hygiene conditions.

By way of example, the protected region can be produced under controlled conditions within the scope of a production process, for example by means of a qualified production process, more particularly a certified production process. By way of example, the protected region can be provided and/or supported by a defined and substantially constant force action, which for example can be configured independently of an alignment and/or positioning and/or storage of the device, for example in contrast to the structure described in WO 2005/002649 A1. By way of example, as described above, this can be brought about by using at least one holder, for example a holder with at least one bearing and at least one counter bearing. In particular, a force can act on the protected region and/or an intermediate element in the protected region, with the container for example being supported on a housing wall of the removal device. This can form at least one contact region, for example with the properties as described above.

The protected region can be delimited in a substantially germ-free fashion with respect to the surroundings, in particular by an embodiment of one or more of the contact areas and/or by using at least one intermediate element. The protected region can in particular permanently have a lower germ load than the surroundings. In particular, the protected region can be produced a long time before the device is used by a user, e.g. a medical practitioner and/or a patient.

By way of example, an optical inspection of the container, which can for example be embodied as primary container for the active ingredient, may count as further processing under these conditions. Alternatively, or in addition thereto, the handling of an associated injection system may also count as part of this further processing, which preferably, on the inside, contains sterile devices for removing the fluid medium out of the container. Hence, neither of the two components necessarily needs to be stored under sterile conditions after production.

The components are preferably only brought together at a later time; this may also occur in non-sterile conditions. Thus, the components may be brought together under non-sterile conditions, wherein, nevertheless, it is possible to produce a permanently sterile or at least almost germ-free interface in the region of the subsequent fluid transfer.

The device produced thus can initially be stored over a relatively long period of time. The required fluid connection via the sterile or almost germ-free interface is preferably only established, without risk, during the application by a medical practitioner or a patient, which application has a time-offset from the production. To this end, the design and the material selection can be adapted such that a permanently almost germ-free or sterile region, e.g. in the form of a gap-free contact area, arises in the region of the fluid connection, i.e. in the protected region.

Here, the sealing element that can be perforated and/or the section that can be perforated can be designed to be wholly or partly deformable, more particularly to be elastic. Accordingly, provision can be made for at least one elastic interface material. This embodiment is particularly preferred if, as illustrated above, use is made of areal pressing for producing the protected region. Thus, for example, it is possible to exert a force onto at least one boundary so that the transition between the boundaries can be designed without gaps.

Before the assembly, the at least one boundary, embodied as above, can additionally be disinfected. Alternatively, or in addition thereto, at least one boundary material can be wholly or partly produced from antimicrobial material, for example by an appropriate material selection and/or coating.

In this constellation, the assembly can more particularly take place under non-sterile conditions, which simplifies the overall production process and can make the device more robust overall.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein.

DETAILED DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

Figure 1:
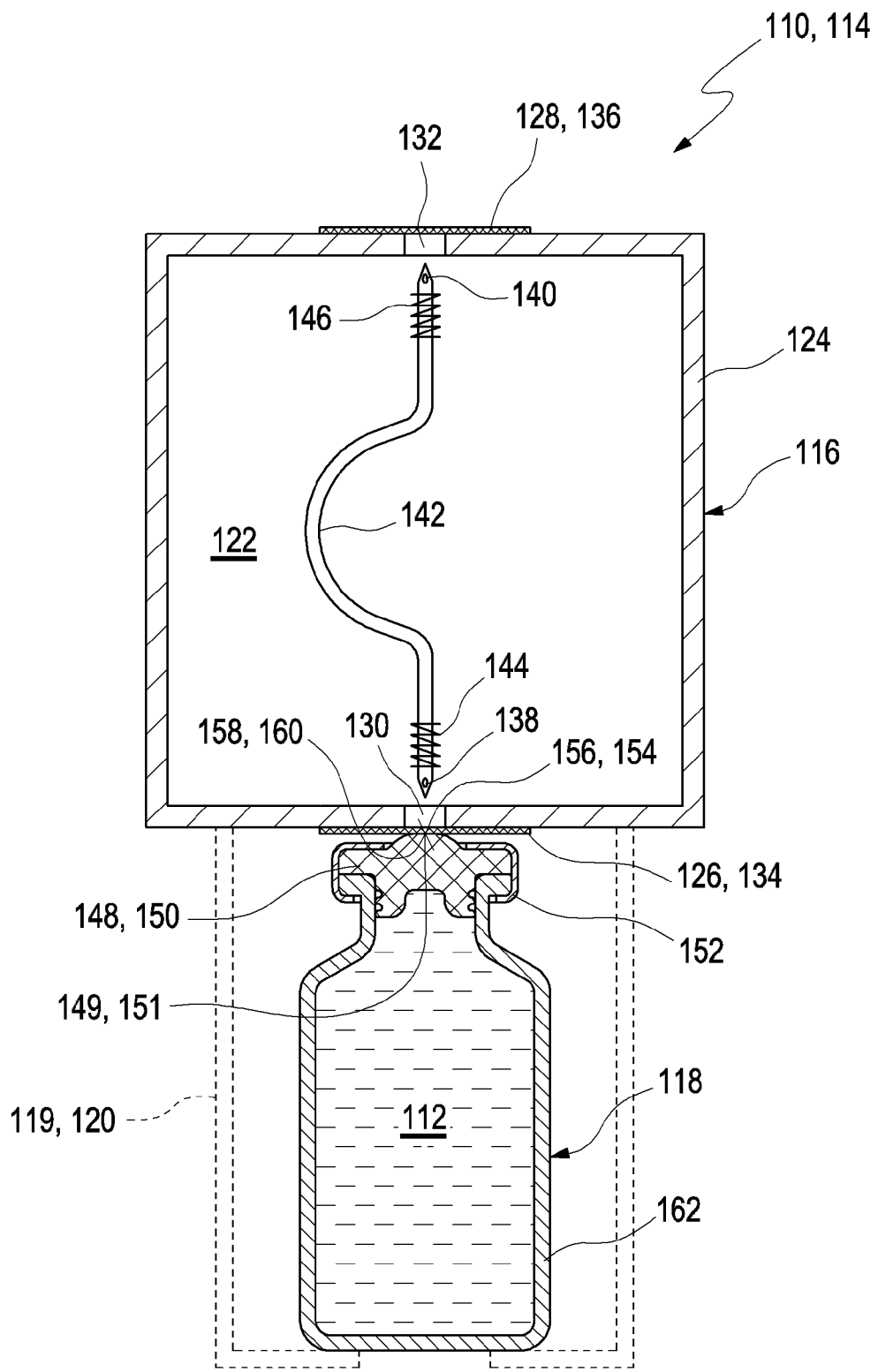
FIG. 1 is a schematic illustration of a device according to one embodiment with a container and a removal device in a connected state.

FIG. 1 illustrates, in a much simplified schematic illustration, a basic design of a device 110 according to one embodiment for providing a fluid medium 112. In this exemplary embodiment, the device 110 is embodied as auto-injector 114. However, in principle, other embodiments are also possible.

In the illustrated exemplary embodiment, the device 110 comprises, as separate components, a removal device 116 and a container 118, which is filled with the fluid medium 112. Although, as indicated in FIG. 1 by a dashed line, the container 118 may be connected to the removal device 116 via at least one holder 119, for example with one or more connection elements 120, there is no fluid connection yet between the removal device 116 and the container 118 in the storage state shown in FIG. 1. As will still be described in the following text, the device 110 is designed only to establish such a fluid connection when the device 110 is used.

The removal device 116 has a sterile or sterilizable interior 122. The latter is surrounded by a wall 124, which is sealed by a first sealing element 126 that can be perforated on the side of the container 118 and by a second sealing element 128 that can be perforated. By way of example, the wall 124 can comprise openings 130, 132, which are closed off by the sealing elements 126, 128 that can be perforated. By way of example, the sealing elements 126, 128 that can be perforated can comprise sealing films 134, 136, which span the openings 130, 132. By way of example, the sealing films 134, 136 can be embodied as films made of plastic and/or metal films.

A first needle element 138 and a second needle element 140 are held within the interior 122. These needle element 138, 140 are merely indicated symbolically in FIG. 1. By way of example, the needle elements 138, 140 can be embodied as cannulae and/or be components of cannulae. By way of example, the needle elements 138, 140 can be mounted in a movable fashion. By way of example, the needle elements 138, 140 can be driven by a drive device to make a piercing movement, more particularly a piercing movement that runs substantially perpendicular to the sealing elements 126, 128 that can be perforated so that the sealing elements 126, 128 can be perforated by means of these movements. The drives of the needle elements 138, 140 are denoted symbolically in FIG. 1 by reference signs 144, 146.

In the exemplary embodiment illustrated using FIG. 1, the device 110 furthermore comprises a fluidic device 142, which is wholly or partly held in the interior 122. This fluidic device 142 is designed to ensure a fluid transport. By way of example, the fluidic device 142 can comprise a tube system with at least one tube and/or another fluid conductor, for example a tube system with one or more tubes made of plastic. However, other embodiments are also possible.

Reference is made to the fact that the embodiment of the removal device 116 in the exemplary embodiment as per FIG. 1 should merely be understood in an exemplary fashion. All that is required in a basic form of the device 110 is the first sealing element 126 that can be perforated and the first needle element 138. The fluid medium can also be provided in another fashion instead of by the second needle element 140, for example via a tube system that is or can be connected to the removal device 116.

Furthermore, provision can be made for additional elements (not illustrated in FIG. 1), for example at least one further drive that allows fluid transport into the interior 122 from the container 118 and/or out of the interior 122, for example via the second needle element 140. However, as will be explained in more detail below, a different type of drive for the fluid transport is also possible.

The container 118 comprises at least one section 148 that can be perforated and that can—directly or indirectly—be connected to the first sealing element 126 that can be perforated. By way of example, in the case of a direct connection, the section 148 that can be perforated and the first sealing element 126 that can be perforated can be in direct contact. However, as an alternative or in addition thereto, an optional space 149 can also be formed (this is indicated in FIG. 1), which preferably has a gap width of zero but which, in principle, can also have a finite width and can optionally be filled and/or protected and/or surrounded by, for example, one or more intermediate elements 151, which are explained in more detail below and merely indicated in FIG. 1. This will still be explained in more detail below in an exemplary fashion.

In the illustrated exemplary embodiment, this section 148 that can be perforated is, in an exemplary fashion, illustrated as a stopper 150. The latter can for example be secured by a flange 152. The flange 152 can also ensure that an external side 154 of the section 148 that can be perforated, for example of the stopper 150, is pre-arched, as can be identified in FIG. 1. By way of example, as shown in FIG. 1, this external side 154 acts as a contact area 156 which can be pressed against an external side 158 of the first sealing element 126 that can be perforated, which external side likewise acts as a contact area 160. By way of example, the connection element 120 can be designed such that the external side 145 of the container 118 is pressed against the external side 158 of the first sealing element 126 that can be perforated. By way of example, this can provide a force fit and/or interlocking connection between the removal device 116 and the container 118.

The container 118 can furthermore comprise a container wall 162, which is made, for example, of a glass material or a material made of plastic. However, in principle, other embodiments are also possible, for example embodiments in which the whole container wall 162 or relatively large sections thereof are embodied as sections 148 that can be perforated.

Figure 2:
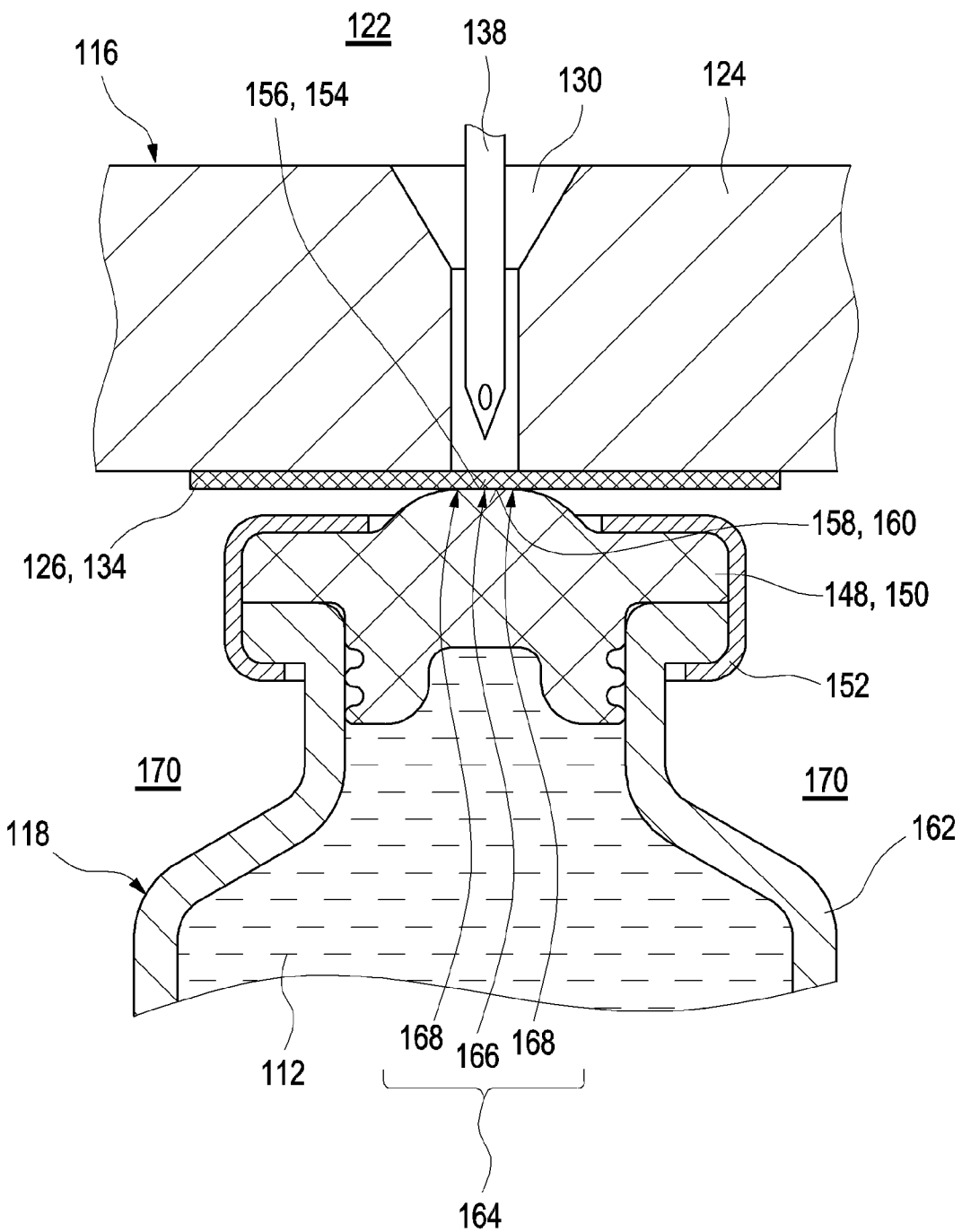
FIGS. 2 to 4 show various detailed illustrations of possible embodiments of a protected region in the region of a connection between a sealing element that can be perforated and the removal device and a section of the container in FIG. 1 that can be perforated.

FIG. 2 shows a magnified illustration of a connection region between the container 118 and the removal device 116 from FIG. 1. An exemplary embodiment emerges from this illustration in particular; here, areal pressing is used for sealing. The contact area 156 of the section 148 that can be perforated is pressed against the contact area 160 of the first sealing element 126 that can be perforated. Here, for example, the opening 130 in the wall 124 of the removal device 116 can be dimensioned such that the diameter thereof is smaller than the area within which the contact areas 156, 160 lie on top of one another. Accordingly, a predominant component of the contact pressure can be taken up by the wall 124, and so the sealing film 134 can be unburdened.

As a result of the areal pressure, a contact region 164 is created in the region of the connection between the first sealing element 126 that can be perforated and the section 148 that can be perforated and, as indicated in FIG. 2, the perforation can occur through said contact region by means of the first needle element 138 at a later stage. Here, the contact region is subdivided, virtually, into an inner, protected region 166, through which the perforation is made, and a barrier region 168, which surrounds this protected region 166 and provides a germ barrier against ingress of germs from the surroundings 170 into the protected region 166. By way of example, the barrier region 168 can surround the protected region 166 in an annular fashion. However, ultimately, the protected region 166 and the barrier region 168 are components of the contact region 164 in this exemplary embodiment. However, this is not necessarily the case, as will be described in more detail using the subsequent exemplary embodiments. The first sealing element 126 that can be perforated and/or the section 148 that can be perforated preferably have a deformable design such that there is at least a partial deformation of at least one of these elements during the connection and during the production of the contact region 164. This deformation increases the area of the contact region 164 and secures the connection.

Using a conventional technique, the components of the device 110 would have to be produced and treated such that these individual components do not leave sterile surroundings until the time at which the removal device 116 and the container 118 are coupled in a sterile fashion. Various components would have to be produced individually under cleanroom conditions and sterilized. The sterile components should thereafter be brought together and assembled to form a sterile unit, which would then, for example, have to be packaged in a germ-tight fashion in order to store it for a relatively long time before the actual application including a perforation of the first sealing element 126 that can be perforated and the section 148 that can be perforated. The disadvantages of this product development substantially consist of the fact that production under sterile conditions is very complicated and cost-intensive. Although this problem can, in principle, be mastered by means of isolators, the production costs increase significantly in respect of the ambient conditions and the material logistics. Moreover, the risk to the quality increases with every step in the process chain that has to be carried out under aseptic conditions without the option of a final sterilization.

By contrast, in the systems proposed in FIGS. 1 and 2, the removal device 116 and container 118 components can be produced separately. By way of example, the removal device 116 can be produced under cleanroom conditions. The interior 122 can be sterilized after being closed off by the sealing elements 126, 128 that can be perforated, for example by means of ionizing radiation such as e.g. γ-radiation and/or β-radiation. However, as an alternative or in addition thereto, there can also be another type of sterilization in this exemplary embodiment or in other exemplary embodiments, for example sterilization by being gassed by a gaseous, germicidal means, e.g. ethylene oxide. The removal device 116 produced thus can then be stored under normal conditions, without needing to take note of increased requirements in respect of freedom from germs. The container 118 can likewise be filled with the fluid medium 112, e.g. by means of a conventional filling system, more particularly under sterile-room conditions. After the container 118 has been closed off, for example by means of the stopper 150 and/or in another fashion, the sterile-room conditions can then be interrupted. Thus, for example, there can be separate interim storage of the filled containers 118. It is also possible for further process steps, such as e.g. an optical inspection, to take place under non-sterile conditions, which opens up significant potential savings in the production costs.

The removal device 116 and the container 118 are then interconnected when the device 110 is assembled, for example as shown in FIGS. 1 and 2. It is possible to disinfect or even sterilize the external side 154 of the section 148 that can be perforated and/or the external side 158 of the first sealing element 126 that can be perforated before and/or during and/or directly after connecting these elements 116, 118 in order to create germ-free initial conditions for the protected region 166. This can efficiently prevent microbial growth in the region of the protected region 166. As illustrated above, there can be various ways of disinfecting. Thus, for example, this can be performed by means of one or more chemical disinfectants that can be applied externally, e.g. isopropanol. Alternatively, or in addition thereto, it is also possible for one or more chemical disinfectants to be wholly or partly integrated into the elements 126 and/or 148. Thus, for example, the first sealing element 126 that can be perforated and/or the section 148 that can be perforated may contain materials that have a germicidal effect. These materials can be provided intrinsically and/or can also be applied as coating to the external sides 154 and/or 158. Examples of such materials are silver or silver iodide particles. By way of example, plastics filled and/or coated with silver iodide can be used for the first sealing element 126 that can be perforated and/or the section 148 that can be perforated.

After the connection between the external sides 154, 158 is established, the device 110 can be stored, for example under conditions that need not satisfy increased demands in respect of being germ-free. Since the contact region 164 is preferably embodied substantially without a gap, the barrier region 168 prevents ingress of germs into the protected region 166 through which the perforation will later take place. By way of example, the barrier region 168 may permit gap widths of at most 10 μm, preferably at most 5 μm or less, more particularly 1 μm or less. By way of example, the connection element 120 can maintain such areal pressing which can ensure this freedom from gaps.

Thus, after separate production of the components 116 and 118 and, for example, after a separate quality control, the proposed method allows a bringing together of these components at a later time under non-sterile conditions. Nevertheless, a permanently almost germ-free or germ-free interface is produced in the region of the later fluid transfer using the proposed method. The required fluid connection via the almost germ-free or germ-free interface is only established later, with no risk of contamination, during the time-offset application by the medical practitioner or the patient by virtue of the fact that the first needle element 138 perforates the protected region 166 and establishes a fluid connection between the inside of the container 118 and the interior 122. Overall, the whole production process can be very much simplified and the device 110 as overall system can have a more robust design.

Reference is made to the fact that the device 110 as per FIG. 1 may also comprise even more components, for example a common housing that wholly or partly surrounds the illustrated components. By way of example, the second sealing element 128 that can be perorated can in this case be embodied such that the latter can be placed onto a tissue surface, e.g. a skin surface of a user, for example a patient. The protected region 166 can subsequently be perforated by means of the drives 144 and/or 146. At the same time, the drive 146 can perforate the second sealing element 128 that can be perforated, followed by a perforation of part of the skin and/or another part of the tissue of the user, and by an injection of the fluid medium 112 into the tissue of the user.

Figure 3:
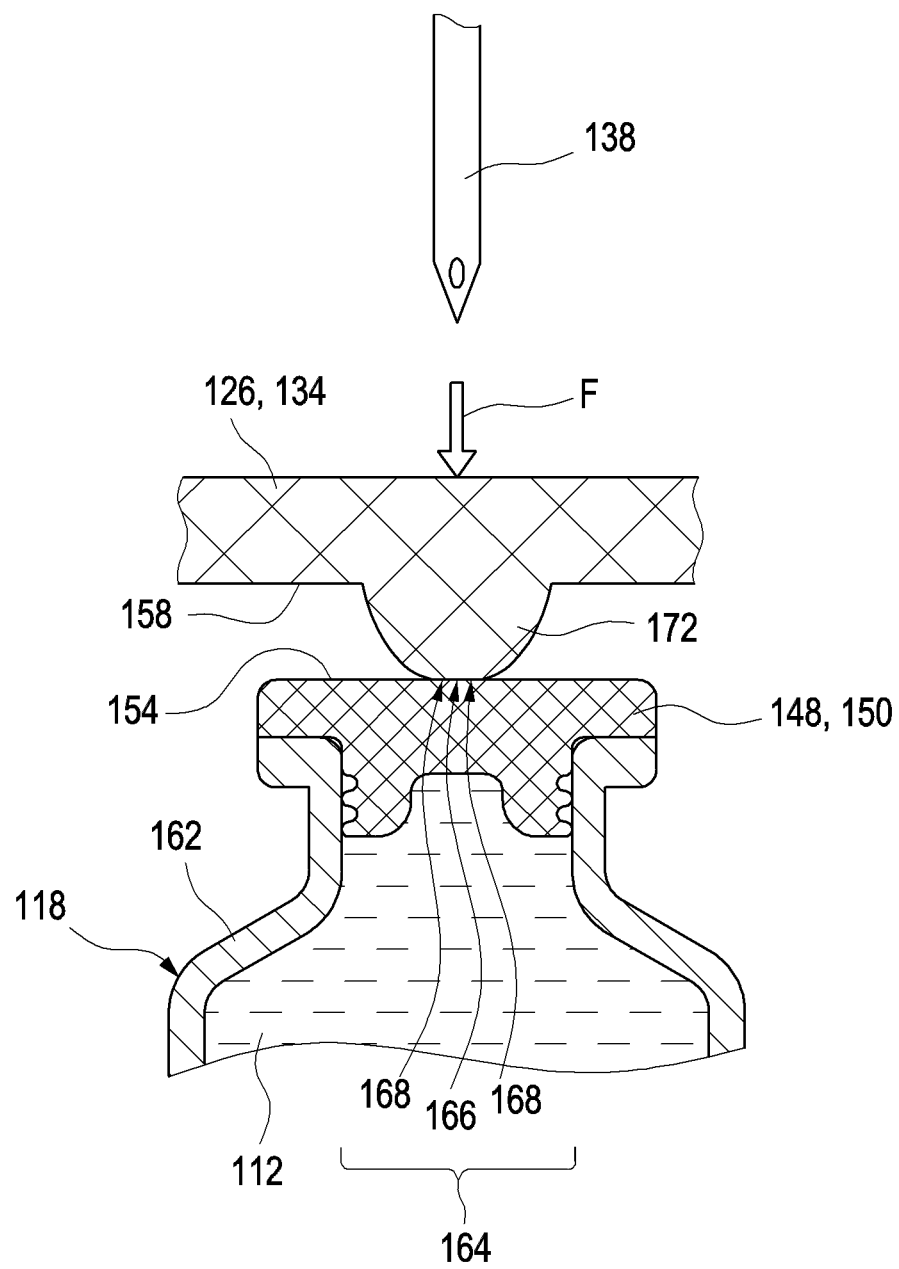
Figure 4:
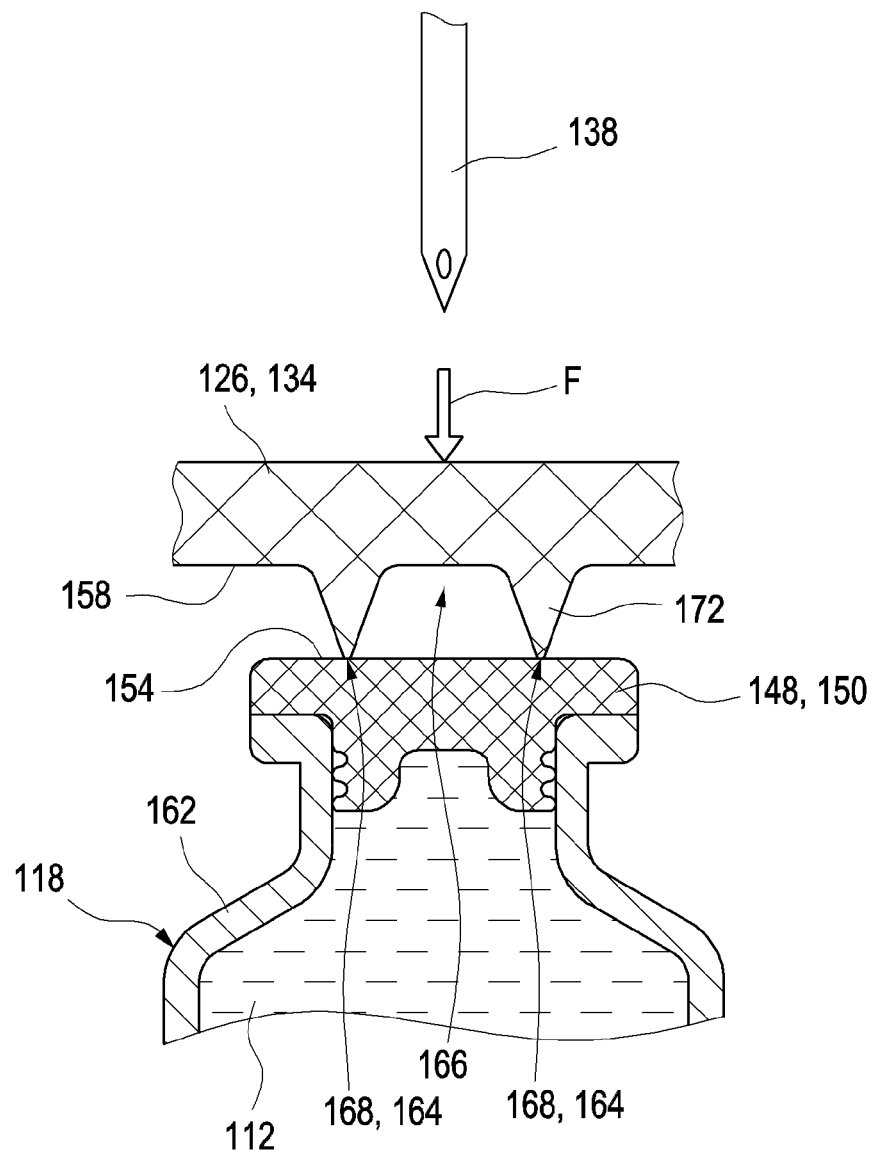

FIGS. 3 and 4 illustrate alternative embodiments of the connection between the first sealing element 126 that can be perforated and the section 148 that can be perforated; these are likewise based on areal pressing using a force F. However, the functional principle is the same in both cases as described above on the basis of FIG. 2. By way of example, the force F can be provided by the connection element 120.

Here, FIG. 3 shows an exemplary embodiment in which the first sealing element 126 that can be perforated comprises a projection 172, i.e. it has a convex design. Thus, overall, it is preferred if at least one of the sealing element 126 that can be perforated and section 148 that can be perforated elements has a convex design. A convex design of both elements is also possible.

While the protected region 166 is part of the areal pressing, and hence a component of the contact region 164, in the embodiments in FIGS. 2 and 3, the exemplary embodiment illustrated in FIG. 4 shows that this does not necessarily have to be the case. In this case, the sealing element 126 that can be perforated once again comprises a projection 172; however, this does not simply comprise a protrusion but rather an annular projection 172 in this exemplary embodiment. Alternatively, or in addition thereto, the section 148 that can be perforated could also comprise such a projection 172 on its external side 154. The projection 172, which in this case has an annular design, surrounds the protected region 166 after the pressing. In this case, areal pressing only takes place in the region in which the projection 172 lies on the external side 154. The contact face in this case also forms a barrier region 168, which, in its interior, seals the protected region 166 in a substantially germ-free fashion.

As an alternative or in addition to the areal pressing illustrated on the basis of FIGS. 2 to 4, there can also be a different way of providing the barrier region 168, which does not necessarily need to be based on a contact force F. Thus, for example, there can also be areal adhesive bonding, by means of which the external sides 154, 158 are adhesively bonded to one another. Here, the protected region 166 may lie within the adhesive bond or at least be surrounded by the adhesive bond such that the adhesive bond forms the barrier region 168. In another alternative or in addition thereto, it is also possible, as illustrated above, to use one or more intermediate elements, e.g. seals. However, the embodiment of the areal pressing without intermediate elements in the form of an adhesive and/or seals between the external sides 154, 158, as illustrated in FIGS. 2 to 4, is particularly preferred since this allows particularly simple assembly.

Figure 6:
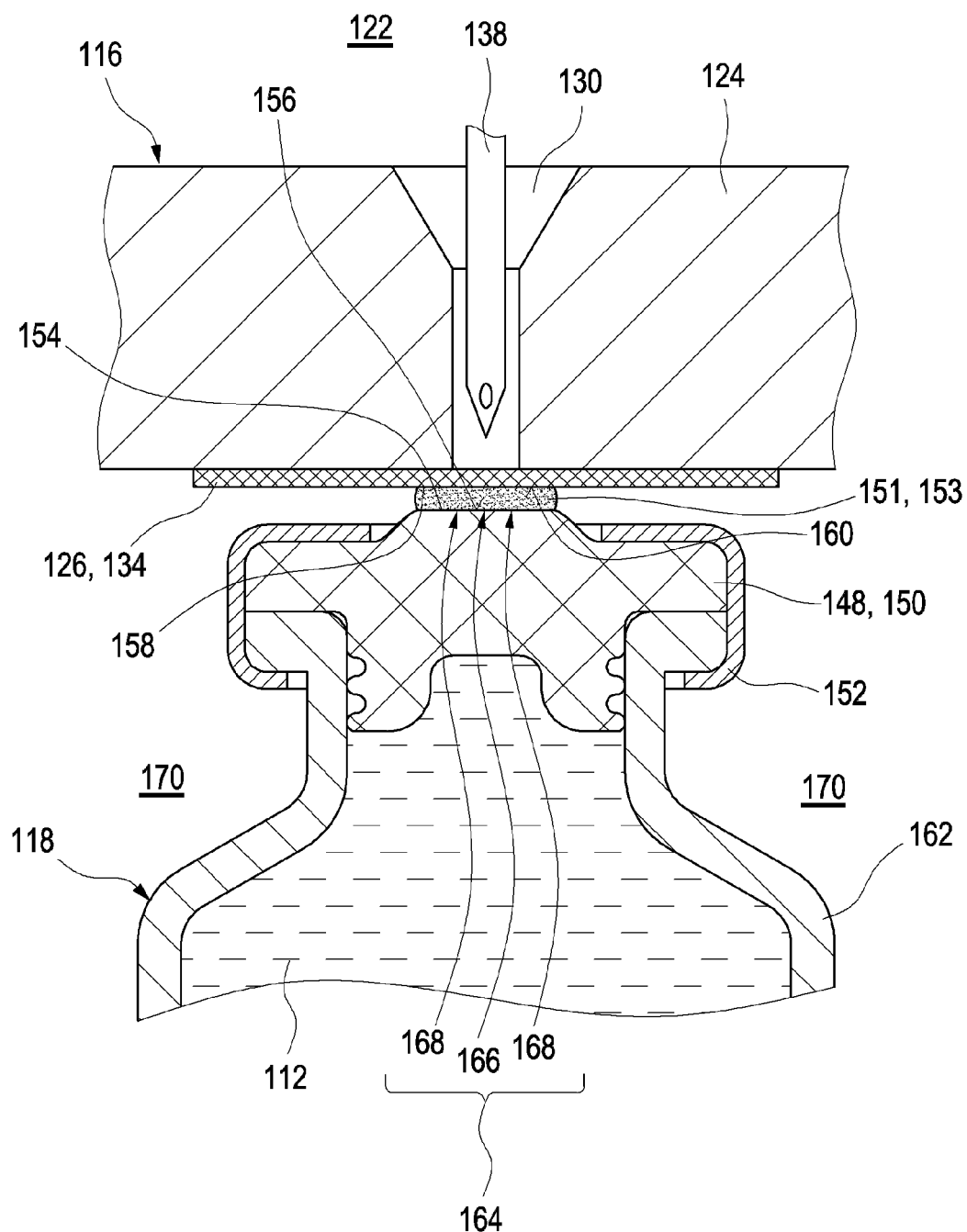
FIGS. 6 and 7 show embodiments of a protected region with at least one intermediate element, which are alternatives to the embodiments in FIGS. 2 to 4.
Figure 7:
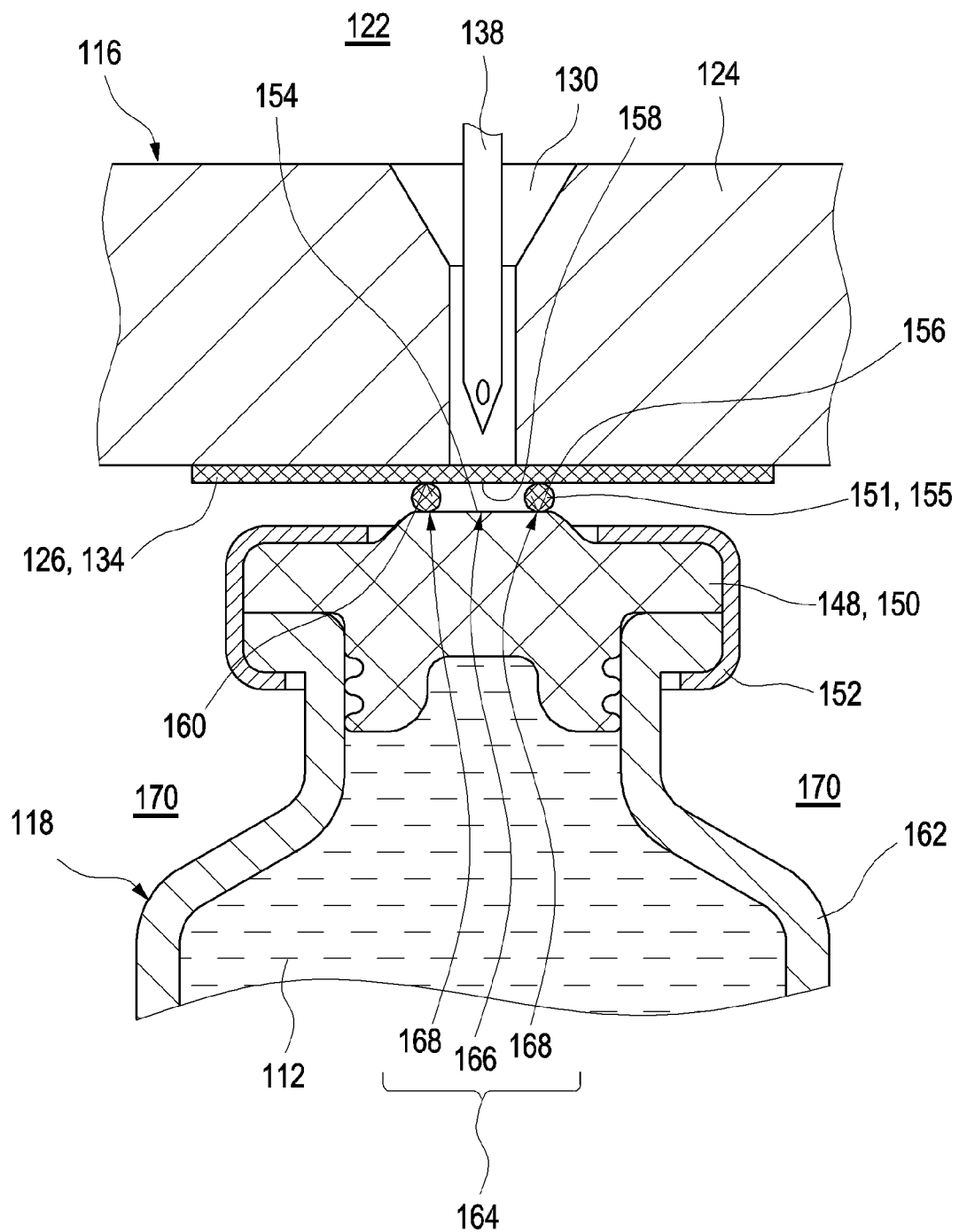

FIGS. 6 and 7 show exemplary embodiments that are alternatives to the ones in FIGS. 2 to 4 and in which at least one intermediate element 151 is introduced between an external side 158 of the sealing element 126 that can be perforated and an external side 154 of the section 148 that can be perforated. In this case, these external sides 154, 158 are connected indirectly via the intermediate element 151. By way of example, contact areas 156, 160 can likewise be formed in this case, for example by once again using a holder 119 with one or more connection elements 120 (not illustrated in FIGS. 6 and 7), wherein, however, the contact areas 156 and 160 may be embodied separately in this exemplary embodiment. By way of example, in this exemplary embodiment the contact area can be formed between the external side 154 of the section 148 that can be perforated and the intermediate element 151, whereas the contact face 160 is formed between the external side 158 of the sealing element 126 that can be perforated and the intermediate element 151.

In the exemplary embodiment illustrated in FIG. 6, the at least one intermediate element 151 is for example embodied in the form of at least one adhesive 153, which extends over the whole protected region 166 and preferably beyond the latter. By way of example, an edge region of this adhesive 153 can thus act as barrier region 168. Here, the term adhesive 153 should be interpreted so broadly that an adhesive may comprise e.g. any material, as described above, which can offer the aforementioned barrier effect.

By contrast, in the exemplary embodiment as per FIG. 7, which, like the exemplary embodiment in FIG. 6 as well, can be combined with other exemplary embodiments as often as desired, the intermediate element 151 by contrast comprises one or more seals 155. By way of example, this at least one seal 155 can comprise one or more O-rings, which can surround the protected region 166 and hence can form a barrier region 166. In this case, the contact area 156 for example is formed between the external side 154 of the section 148 that can be perforated and the seal 155, and the contact area 160 is for example formed between the external side 158 of the sealing element 126 and the seal 155. Like in the embodiment of the intermediate element 155 as adhesive 153 as per FIG. 6 as well, it is also optionally possible to provide at least one holder 119 in the exemplary embodiment as per FIG. 7, for example with at least one connection element 120 in order e.g. to ensure a contact force, preferably a constant contact force.

Figure 5:
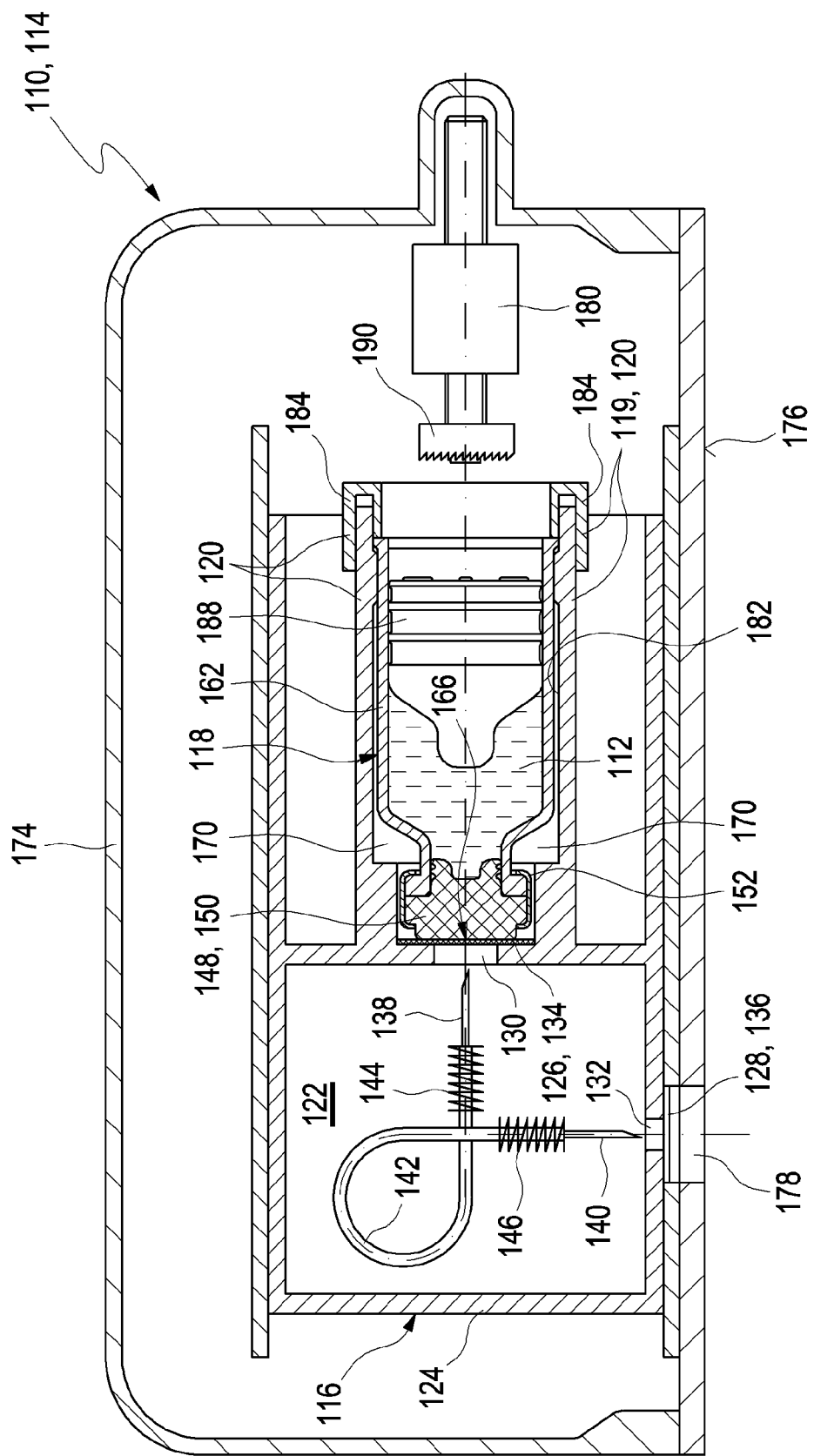
FIG. 5 shows an exemplary embodiment of a device in the form of an auto-injector.

Finally, FIG. 5 shows a more complex exemplary embodiment of a device 110 according to this disclosure. In large part, reference can be made to the description of FIG. 1 in respect of the function of this exemplary embodiment, in which the device 110 is once again embodied as an auto-injector 114. The device 110 comprises a housing 174 with a bearing face 176. This housing 174 holds a removal device 116, for example as per the type described in FIG. 1, wherein reference can largely be made to the description above in respect of the embodiment thereof. The removal device 116 is arranged in the housing 174 such that the second needle element 140 can perforate the skin of a user through the opening 132 and the second sealing element 128 that can be perforated and through a further opening 178 in the housing 174 in order to inject a fluid medium 112 into a tissue of a user.

Here, this can in principle be any type of injection. However, a subcutaneous injection is typical, more particularly a subcutaneous injection into a body tissue outside of the blood vessels over a relatively long period of time. By way of example, the injection process may stretch over a number of minutes up to a number of hours, and it is possible for relatively large amounts of fluid medium 112 to be injected.

An assembly of the device 110, including the removal device 116 and remaining parts, for example a further drive 180, can, as described above, take place independently of a container 118 that can be held in the device 110 being filled. In the process, there can also be a sterilization of an interior 122 of the removal device 116. The container 118 and the device 110 prepared thus are subsequently brought together, with a section 148 that can be perforated of the container 118 and the first sealing element 126 that can be perforated of the removal device 116 being connected. In respect of this connection, reference can for example be made to the above description of FIGS. 2 to 4. By way of example, provision can once again be made for at least one holder 119 with at least one connection element 120. On the one hand, this can provide a receptacle 182 for holding the container 118, which can for example have an appropriate shape. Furthermore, the connection element 120 can comprise one or more contact elements 184, by means of which a contact force can be provided. By way of example, these may be union nuts, screw elements, elastic clamping elements or the like. In principle, a person skilled in the art is aware of such contact elements 184.

As illustrated above, this connection produces a protected region 166, through which the perforation and the establishment of the fluid connection between the interior of the container 118 and the interior 122 can be established later. As a result of the connection, the protected region 166 is protected against ingress of germs from the surroundings 170, and so even relatively long storage is possible. It is possible to dispense with sealing the receptacle 182, for example in the form of a sealing film, and so the interior of the receptacle 182 may be part of the surroundings 170 and hence it need not be embodied in a germ-free fashion.

In the illustrated exemplary embodiment, the container 118 has a further stopper in the form of a plunger stopper 188. The latter is mounted in the container 118 in a moveable fashion. By way of example, the drive 180 has a drive tappet 190 that can move linearly and interact with the plunger stopper 188 in order to drive the latter into the interior of the container 118 and generate positive pressure there.

The device 110 as per FIG. 5 can for example be used such that it is placed onto a skin surface with the bearing face 176. Subsequently, there is—either simultaneously or with a time offset—a perforation of the protected region 166 by means of the first needle element 138 and a perforation of the second sealing element 128 that can be perforated and the skin surface of the user by means of the second needle element 140. There is an actuation of the drive 180 and an increase in the internal pressure of the container 118; this once again occurs simultaneously or with a time offset. This transfers fluid medium 112 into the fluidic device 142 and, from the latter, into the body tissue and/or the blood vessel of the patient.

The exemplary embodiment in FIG. 5 shows that the device 110 can have a comparatively complex design. By way of example, provision can additionally be made for a control, which synchronizes the actuation of the drives 144, 146 and 180. Thus, overall, the device 110 can obtain a complicated electromechanical and/or fluidic embodiment, which requires a thorough inspection of function and/or quality. Such an embodiment would be almost impossible in the case of complete assembly under sterile conditions.

While exemplary embodiments incorporating the principles of the present invention have been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

LIST OF REFERENCE SIGNS

110 Device for providing a fluid medium
112 Fluid medium
114 Auto-injector
116 Removal device
118 Container
119 Holder
120 Connection element
122 Interior
124 Wall
126 First sealing element that can be perforated
128 Second sealing element that can be perforated
130 Opening
132 Opening
134 Sealing film
136 Sealing film
138 First needle element
140 Second needle element
142 Fluidic device
144 Drive
146 Drive
148 Section that can be perforated
149 Space
150 Stopper
151 Intermediate element
152 Flange
153 Adhesive
154 External side
155 Seal
156 Contact area
158 External side
160 Contact area
162 Container wall
164 Contact region
166 Protected region
168 Barrier region
170 Surroundings
172 Projection
174 Housing
176 Bearing face
178 Opening
180 Drive
182 Receptacle
184 Contact element
188 Plunger stopper
190 Drive tappet

What is claimed is:

1. A method for removing a fluid medium from a container, comprising the following steps:
   (a) providing a removal device with a closed-off, sterilizable interior, at least one needle element being held in the interior and the interior being closed off by at least one germ-blocking perforable sealing element;

(b) providing the container which contains the fluid medium, the container having at least one container wall with at least one perforable section;
(c) connecting the removal device and the container, wherein the connecting produces a protected region between the perforable section and the perforable sealing element, the protected region being closed off to the surroundings in a substantially germ-tight fashion; and
(d) perforating the perforable sealing element and the perforable section with a needle element, wherein the needle element penetrates the protected region;
wherein a period of time of at least one week passes between step (c) and step (d).

2. The method of claim 1, wherein in step (b), the fluid medium is introduced into the container in sterile surroundings, wherein method step (c) is subsequently carried out in non-sterile surroundings.

3. The method of claim 1, wherein at least one processing step is carried out before method step (c), wherein, during the processing step, at least one element of the group consisting of an external side of the perforable sealing element, an external side of the perforable section and a space between the perforable sealing element and the perforable section is protected against germ contamination.

4. The method of claim 3, wherein the processing step comprises at least one disinfection step comprising an external side of the perforable sealing element and/or an external side of the perforable section being at least partly disinfected and/or sterilized.

5. The method of claim 4, wherein the disinfection and/or sterilization comprises one or more of the following methods: a thermal disinfection and/or sterilization; a disinfection and/or sterilization by ionizing radiation; a chemical disinfection and/or sterilization; a chemical disinfection by at least one germicide held in the perforable sealing element and/or in the perforable section.

6. The method of claim 1, further comprising introducing an intermediate element between the external side of the perforable sealing element and the external side of the perforable section before carrying out step (c), whereby the intermediate element provides a germ barrier for the protected region.

7. The method of claim 6, wherein the intermediate element comprises at least one element selected from the group consisting of an adhesive and a seal.

8. The method of claim 1, wherein the removal device and the container are connected such that the perforable section and the perforable sealing element are pressed against one another with a predefined contact force.

9. The method of claim 1, wherein the container is filled with the fluid medium and closed off under substantially germ-free conditions before step (b), the substantially germ-free conditions being interrupted after filling and before step (c).

10. The method of claim 1, wherein the interior is disinfected and/or sterilized after closing-off the interior.

11. The method of claim 1, wherein the protected region is closed-off with respect to the surroundings by one or more of the following method steps:
the perforable section is pressed against the perforable sealing element, the protected region being part of a contact region that is created during the pressing and being surrounded by a further part of the contact region that acts as a germ barrier;
the perforable section is pressed against the perforable sealing element, the protected region being surrounded by a contact region created during the pressing, the contact region acting as a germ barrier.

12. The method of claim 1, wherein a period of time of at least 1 month passes between step (c) and step (d).

13. The method of claim 1, wherein a period of time of at least 2 months passes between step (c) and step (d).

14. The method of claim 1, further comprising the following step:
(e) the fluid medium is wholly or partly transferred into the interior or through the interior from the container.

15. The method of claim 14, further comprising the following step:
(f) the fluid medium is wholly or partly transported out of the interior or through the interior by a further needle element and/or a cannula that perforates at least one further sealing element that closes off the interior.

16. A device for providing a fluid medium, comprising:
a removal device with a closed-off, sterilizable interior, a needle element being held in the interior, and the interior being closed off by a germ-blocking perforable sealing element;
a container containing the fluid medium, the container having a container wall with a perforable section;
wherein the removal device and the container are connectable, wherein connecting the perforable section and the perforable sealing element creates a protected region between the perforable section and the perforable sealing element, the connection closing off the protected region with respect to the surroundings in a substantially germ-tight fashion, wherein, in the connected state, the needle element is capable of perforating the perforable sealing element and the perforable section such that the needle element penetrates the protected region; and
further wherein, in the connected state an intermediate element is disposed between the external side of the perforable sealing element and the external side of the perforable section, the intermediate element comprising a germ barrier for the protected region.

17. The device of claim 16, wherein, in the connected state, microbial growth is substantially prevented in the protected region.

18. The device of claim 16, wherein the intermediate element comprises at least one element selected from the group consisting of an adhesive and a seal.

19. The device of claim 16, wherein in the connected state, the perforable section and the perforable sealing element are pressed against one another with a predefined contact force.

20. The device of claim 19, further comprising a holder that provides the predefined contact force.

21. The device of claim 16, wherein the perforable section and/or the perforable sealing element contains at least one material with at least one germicide.

22. The device of claim 21, wherein the germicide comprises silver and/or silver iodide.

23. The device of claim 16, wherein the perforable section and/or the perforable sealing element are deformable.

24. The device of claim 23, wherein the perforable section and/or the perforable sealing element are elastic.

25. The device of claim 17, wherein the needle element is configured to transport the fluid medium wholly or partly into the interior or through the interior from the container.

26. The device of claim 25, wherein the needle element is configured to transport the fluid medium wholly or partly out of the interior by means of a further needle element and/or a cannula.

27. The device of claim 25, further comprising an actuator configured to drive a transfer of the fluid medium into the interior and/or through the interior from the container.

* * * * *